(12) United States Patent
Lin et al.

(10) Patent No.: US 8,153,861 B2
(45) Date of Patent: Apr. 10, 2012

(54) GENES FOR IMPROVING SALT TOLERANCE AND DROUGHT TOLERANCE OF PLANT AND THE USES THEREOF

(75) Inventors: Min Lin, Beijing (CN); Ming Chen, Beijing (CN); Jin Wang, Beijing (CN); Jie Pan, Beijing (CN); Zhengfu Zhou, Beijing (CN); Wei Zhang, Beijing (CN); Wei Lu, Beijing (CN); Shuzhen Ping, Beijing (CN)

(73) Assignee: Biotechnology Research Institute, The Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 12/739,168

(22) PCT Filed: Nov. 9, 2007

(86) PCT No.: PCT/CN2007/071043
§ 371 (c)(1),
(2), (4) Date: Dec. 30, 2010

(87) PCT Pub. No.: WO2009/052687
PCT Pub. Date: Apr. 30, 2009

(65) Prior Publication Data
US 2011/0088121 A1    Apr. 14, 2011

(30) Foreign Application Priority Data

Oct. 22, 2007    (CN) .......................... 2007 1 0176153

(51) Int. Cl.
*A01H 5/00*    (2006.01)
*C12N 15/82*    (2006.01)
(52) U.S. Cl. ..................... 800/289; 800/298; 424/93.2
(58) Field of Classification Search .................... None
See application file for complete search history.

(56) References Cited

U.S. PATENT DOCUMENTS

| | | | |
|---|---|---|---|
| 6,451,977 B1 * | 9/2002 | de Sauvage et al. | 530/350 |
| 6,706,952 B1 * | 3/2004 | Cad et al. | 800/301 |
| 2003/0143707 A1 | 7/2003 | Narumi et al. | |

OTHER PUBLICATIONS

White el al (Science,Nov. 19, 1999;286(5444):1571-7).*
GenBank AE000513.1, available Dec. 2000.*
Gen Bank NP293891.1, available Dec. 2000.*
EMBL Accession No. AAF09762.1, May 1, 2000.
Owen White et al. "*Deinococcus radiodurans* R1 Genome Sequence of the Radioresistant Bacterium", *Science*, vol. 286, pp. 1571-1576 (1999).
Kira S. Makarova et al., "Genome of the Extremely Radiation-Resistant Bacterium *Deinoccoccus radiodurans* Viewed from the Perspective of Comparative Genomics", *Microbiology and Molecular Biology Reviews*, vol. 65, No. 1, pp. 44-79 (2001).
Hua Yuejin et al., "Comparative Genomics of Genes Contributed to DNA Repair in the Radiation-resistant *Deinococcus radiodurans,*" *Acta Microbiologica Sinica*, vol. 3, No. 1, pp. 120-125 (2003).
Valerie Mattimore et al., Radioresistance of *Deinococcus radiodurans*: Functions Necessary to Survive Ionizing Radiation Are Also Necessary to Survive Prolonged Desiccation, *Journal of Bacteriology*, vol. 178, No. 3, p. 633-637 (1996).

* cited by examiner

*Primary Examiner* — Anne Kubelik
*Assistant Examiner* — Lee Visone
(74) *Attorney, Agent, or Firm* — Drinker Biddle & Reath LLP

(57) ABSTRACT

A gene comprising the nucleic acid sequence of SEQ ID NO:1 and another gene comprising the nucleic acid sequence of SEQ ID NO:2, the latter being artificially synthesized according to plant preferred codons. Both genes encode a protein having the amino acid sequence of SEQ ID NO:3. Also provided are recombinant vectors containing each of the genes and host cells transformed with the recombinant vectors. The host cells can be prokaryotic cells [[and]] or eukaryotic cells. The transgenic plants comprising the gene having the nucleic acid sequence of SEQ ID NO:2 show improved salt and drought tolerance after the [[said]] gene is expressed in the transgenic plants.

7 Claims, 2 Drawing Sheets

Fig. 4
Fig. 5
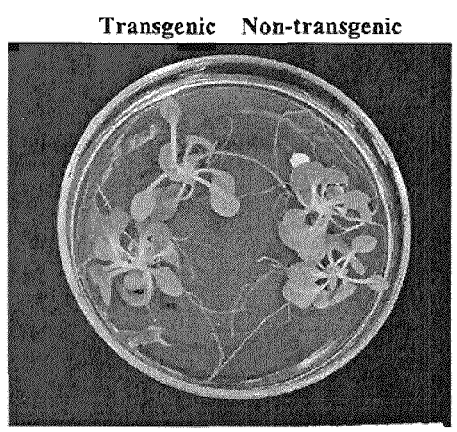 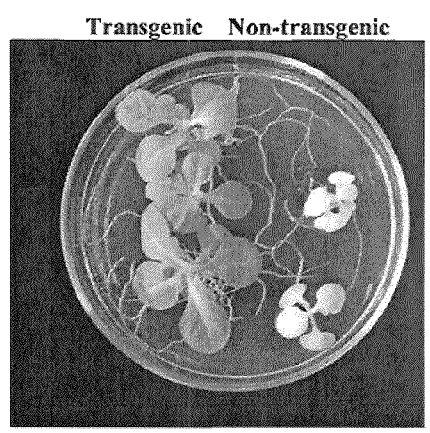
Fig. 6               Fig. 7

US 8,153,861 B2

GENES FOR IMPROVING SALT TOLERANCE AND DROUGHT TOLERANCE OF PLANT AND THE USES THEREOF

TECHNICAL FIELD

The invention relates to a nucleic acid sequence and another nucleic acid sequence artificially synthesized according to plant preferred codons. The invention also relates to the application of the said nucleic acids in plants to improve salt tolerance and drought tolerance.

BACKGROUND ART

*Deinococcus radiodurans* (*D. radiodurans*) is one of the organisms having the highest radiation resistance known so far. The bacterium has a extremely high resistance to lethal doses of radiation ionizing, UV radiation and DNA damaging agents, and is capable of repairing a genome having hundreds DNA double-strand breaks caused by radiation ionizing without any mutation. There have been great interests in the scientific fields on its extraordinary radiation resistance and its repair mechanisms for DNA damage. These features are important for basic researches on DNA repair mechanisms and have potential application prospects in environmental protection, bioremediation, human health, biotechnology, or even exploration and development of the outer space. The institute for Genomic Research (TIGR) completed and published the whole genome sequence of *D. radiodurans* in 1999.

There has been no report in the art on any application using *Deinococcus radiodurans* in plants to improve salt tolerance and drought tolerance.

DISCLOSURE OF THE INVENTION

An aim of the invention is to find and artificially synthesize the DNA sequences for improving salt tolerance and drought tolerance of plants, transfer the sequences into plants and grow the transgenic plants having improved salt and drought tolerance.

The inventors found the DNA sequences set forth in SEQ ID NO:1 and SEQ ID NO:2, both of which are capable of improve salt and drought tolerance in plants. SEQ ID NO:1 is derived from a region of *D. radiodurans*; while SEQ ID NO:2 is derived from SEQ ID NO:1 and artificially synthesized according to plant preferred codons.

The invention also provides a recombinant vector, comprising DNA set forth in SEQ ID NO:1 or DNA set forth in SEQ ID NO:2. The host cells are transformed with the said recombinant vector and the host cells include prokaryotic cell and eukaryotic cell. The prokaryotic host cells commonly used include JM109 and the eukaryotic host cells commonly used include yeast cells and other plant cells. In an embodiment of the invention, the host cells are *E. coli* JM109 cells or tobacco cells.

In an aspect of the invention, it also provides a method for generating a polypeptide encoded by SEQ ID NO:1 or SEQ ID NO:2, comprising the steps of:

(1) operatively linking a nucleic acid having the sequence of SEQ ID NO:1 or SEQ ID NO:2 to an expression regulation sequence to form a protein expression vector;

(2) transforming the expression vector of the step (1) into host cells to form recombinant cells;

(3) culturing the recombinant cells from the step (2) under the condition suitable for the expression of the polypeptide encoded by SEQ ID NO:1 or SEQ ID NO:2;

(4) isolating a substantially pure polypeptide having the amino acid sequence of SEQ ID NO:3.

The invention further provides a method of transforming a nucleic acid having the sequence of SEQ ID NO:1 or SEQ ID NO:2 into a plant using transgenic technology to improve salt tolerance and drought tolerance of the transgenic plant, comprising the steps of:

(1) operatively linking a nucleic acid having the sequence of SEQ ID NO:1 or SEQ ID NO:2 to a plant expression regulation sequence to form a plant expression vector;

(2) transforming the expression vector of the step (1) into plant cells;

(3) obtaining the transformed cells via screening and regenerating the transformed cells into transgenic plants and progenies thereof, including seeds and tissues of the transgenic plants.

The term "operatively linked to" as described above means, i.e. a certain region of a linear DNA sequence is able to influence the function of the remaining region of the same linear DNA sequence. For example, a DNA encoding a signal peptide (secretion leader sequence) is operatively linked to a DNA encoding a polypeptide if the encoded signal peptide is expressed as a precursor and participates in the secretion of the polypeptide; a promoter is operatively linked to the coding sequence if the transcription of the coding sequence is controlled by the promoter; and a ribosome binding site is operatively linked to a coding sequence if the ribosome binding site is positioned such that the coding sequence is translated. In general, the term "operatively linked to" means to be adjacent, and to be adjacent in reading frames for the secretion leader sequence.

In one embodiment of the invention, the expression vector of step (1) is transformed into *Agrobacterium*, *Agrobacterium* containing the expression vector is co-cultured with eukaryotic host cells at 22-28° C., the transformed host cells containing SEQ ID NO:1 or SEQ ID NO:2 gene are obtained via screening such as antibiotics screening after dark cultivation for 1-2 days, and the transformed host cells are regenerated into transgenic plants and progenies thereof, including seeds and tissues of the transgenic plants.

It is confirmed by experiments that the transgenic plants as described above exhibit improved salt and drought tolerance.

The vectors as described above may be selected from various vectors known in the art, for example, commercially available vectors, including plasmids and cosmids and the like.

In addition, the invention further provides a nucleic acid which can be used as a probe. The probe generally has 8-100 consecutive nucleotides of SEQ ID NO:1 or SEQ ID NO:2, preferably 5-15 consecutive nucleotides. The probe may be used to detect whether a nucleic acid molecule comprising the sequence of SEQ ID NO:1 or SEQ ID NO:2 is present in a sample.

The invention also provides a method for detecting whether a nucleic acid molecule comprising the sequence of SEQ ID NO:1 or SEQ ID NO:2 is present in a sample, comprising hybridizing the sample with the probe as described above and then determining whether the probe binds. Preferably, the sample is a PCR amplification product, wherein the primers for the PCR amplification correspond to SEQ ID NO:1 or SEQ ID NO:2 and may flank the sequence or be in the middle of the sequence. The primer is generally 15-50 nucleotides in length.

In the invention, "SEQ ID NO:1 or SEQ ID NO:2" refers to a nucleotide sequence coding a polypeptide encoded by SEQ ID NO:1 or SEQ ID NO:2 and a degenerate sequence thereof. The degenerate sequence refers to a sequence where one or more codons are substituted with the corresponding degenerate codons coding the same amino acid(s). A degenerate sequence having a homology as low as about 89% with SEQ ID NO:1 or SEQ ID NO:2 also may code the polypeptide encoded by SEQ ID NO:2. The term also includes a nucleotide sequence hybridizable with the nucleotide sequence of SEQ ID NO:1 under moderate stringent conditions, preferably under high stringent conditions. The term further includes a nucleotide sequence having 89% homology with the nucleotide sequence of SEQ ID NO:1, preferably at least 80%, more preferably at least 90%, most preferably at least 95%.

The term also includes a variant of the open reading frame sequence of SEQ ID NO:1, wherein the variant encodes a protein having the same function as the one encoded by natural SEQ ID NO:1 or SEQ ID NO:2. These variants include, but are not limited to, those having several (generally 1-90, preferably 1-60, more preferably 1-20, most preferably 1-10) nucleotides deletion, insertion and/or substitution, as well as additional several (generally within 60, preferably within 30, more preferably within 10, most preferably within 5) nucleotides at the 5' and/or 3' end.

In the invention, a "substantially pure" protein or polypeptide means that the protein or polypeptide accounts for at least 20% of the sample, preferably at least 50%, more preferably at least 80%, most preferably at least 90% (the percentage can be based on dry weight or wet weight). The purity can be measured by any suitable method, such as column chromatography, PAGE or HPLC. A substantially pure polypeptide may be generally free of any component that naturally accompanies with the polypeptide.

In the invention, SEQ ID NO:3 protein or polypeptide refers to a polypeptide having the activity of the protein coded by SEQ ID NO:1, also includes a variant having the same function as the protein having the amino acid sequence of SEQ ID NO:3. The variants include, but are not limited to, several (generally 1-90, preferably 1-60, more preferably 1-20, most preferably 1-10) amino acids deletion, insertion and/or substitution, as well as additional several (generally within 60, preferably within 30, more preferably within 10, most preferably within 5) amino acids at the N-terminus and/or C-terminus. For example, in the said proteins, the function of the protein generally is not varied when an amino acid is substituted by another having close or similar properties. In another example, the function of the protein generally may not be varied by adding one or more amino acids at the C-terminus and/or N-terminus. The term also includes an active fragment or an active derivative of SEQ ID NO:3 protein.

The variants of SEQ ID NO:3 polypeptide of the invention include: homologous sequences, conservative variants, allelic variants, natural variants, induction variants, proteins coded by DNA hybridized with SEQ ID NO:1 or SEQ ID NO:2 under high or low stringent conditions and polypeptides and proteins obtained by using antiserum that recognizes a polypeptide having the amino acid sequence of SEQ ID NO:3. The invention also provides other polypeptides, such as a fusion protein containing a polypeptide having the amino acid sequence of SEQ ID NO:3 or a fragment thereof. In addition to a polypeptide of almost full length, the invention also includes a soluble fragment of a polypeptide having the amino acid sequence of SEQ ID NO:3. The fragment generally may have at least about 10 consecutive amino acids, generally at least about 30 consecutive amino acids, preferably at least about 50 consecutive amino acids, more preferably at least about 80 consecutive amino acids, most preferably at least about 100 consecutive amino acids.

In the invention, "SEQ ID NO:3 conservative variant polypeptides" refer to the polypeptides having at most 10, preferably at most 8, more preferably at most 5 amino acids substituted with amino acids having close or similar properties compared to the polypeptide having the amino acid sequence of SEQ ID NO:3. The conservation variant polypeptides can be prepared with the substitutions according to table 1 as below.

TABLE 1 amino acid substitution

| Original residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The invention also embraces an analog of the protein or polypeptide having the amino acid sequence of SEQ ID NO:3. The differences between the analog and the natural polypeptide having the amino acid sequence of SEQ ID NO:3 may be the differences as to the amino acid sequences, or the differences as to modifications that are irrelevant of amino acid sequences, or both. These polypeptides include natural or induced genetic variants. The induced variants can be obtained by various methods, such as random mutagenesis via radiation or exposing to a mutagenic agent, or via site-directed mutagenesis or any other molecular biology techniques known in the art. The analogs also include those containing amino acid residues other than the natural L-amino acids (such as D-amino acids) and those containing non-naturally occurring or synthetic amino acids (such as β, γ-amino acids). It should be understood that the polypeptides of the invention aren't limited to the representative polypeptides as described above.

The modification (the primary structure is generally not modified) may include: chemical modification of polypeptides in vivo or in vitro, such as acetylation or acylation. The modifications also include glycosylation, for example, the polypeptides are produced by glycosylation during the synthesis and/or further processing steps of polypeptides. The modification can be accomplished by exposing the polypeptides to glycosylation enzymes (such as mammalian glycosidases or deglycosidases). The modification also includes phosphorylated amino acid residues (phosphotyrosine, phosphoserine and phosphothreonine). A modified polypeptide having improved resistance to hydrolysis or optimized solubility is also included.

The expression of the gene products from a nucleic acid having the sequence of SEQ ID NO:1 or SEQ ID NO:2 can be analyzed using the Northern bolt method, i.e. to analyze whether the RNA transcripts of SEQ ID NO:1 or SEQ ID NO:2 is present in the cells and to determine the amount thereof.

The Northern blot analysis of RNA of SEQ ID NO:1 or SEQ ID NO:2 and the Western blot analysis using a specific antibody to the polypeptide having the amino acid sequence of SEQ ID NO:3 can be combined, to confirm the expression of SEQ ID NO:1 or SEQ ID NO:2 in a biological sample.

In addition, it is possible to screen and obtain nucleic acids homologous to SEQ ID NO:1 or SEQ ID NO:2, or proteins homologous to that encoded by SEQ ID NO:1 or SEQ ID NO:2.

To obtain a dot matrix of *D. radiodurans* cDNA that is related to the gene of SEQ ID NO:1 or SEQ ID NO:2, *D. radiodurans* cDNA may be screened using a DNA probe under low stringency conditions, wherein the probe can be produced by radioactively labeling the whole or partial SEQ ID NO:1 or SEQ ID NO:2 with 32P. The most suitable cDNA library to be screened is a *D. radiodurans* library. The methods for constructing cDNA libraries from cells or tissues of interest are well known in the field of molecular biology. In addition, many of such libraries may be commercially available, for example, from Clontech, Stratagene, Palo Alto, Calif. The screening methods can identify a nucleotide sequence belonging to a gene family which is related to SEQ ID NO:1 or SEQ ID NO:2.

Once identified, a related sequence can be obtained in a large scale using recombinant DNA methods. Generally, the related sequence is to be cloned into a vector and transformed into a cell. Then, the related sequence can be isolated from the host cells after proliferation by conventional methods.

In addition, a related sequence can also be artificially synthesized by chemical methods. For example, according to knowledge in the art prior to the invention, a plurality of small fragments of polynucleotide may be firstly synthesized and then they may be linked to give the nucleotide sequences coding for SEQ ID NO:3 protein of *D. radiodurans* of the invention. The nucleotide sequences can be subsequently introduced into various exiting DNA molecules (such as a vector) and cells known in the art. Also, mutation(s) can be introduced into the protein-coding sequences of the invention by chemical synthesis.

In addition to the recombinant method, the fragments of the protein of the invention can be produced through solid phase method and direct peptide synthesis (Stewart et al. (1969), Solid-Phase Synthesis, WH Freeman Co., San Francisco; Merrifield J. (1963) Am. Chem. Soc 85:2149-2154). The synthesis of protein in vitro may be performed manually or automatically. For example, the peptides can be synthesized using a 431A Model Peptide Synthesizer from Applied Biosytems (Foster City, Calif.). The respective fragments of the protein of the invention can be chemically synthesized and then they are linked into the full-length molecule by chemical methods.

No.1 is *E. coli* JM109 strain.

No.2 is *E. coli* containing the empty pMD18T vector.

No.3, 4 and 5 are *E. coli* JM109 strains containing the expression vector comprising the SEQ ID NO:1 sequence.

Figure 2:
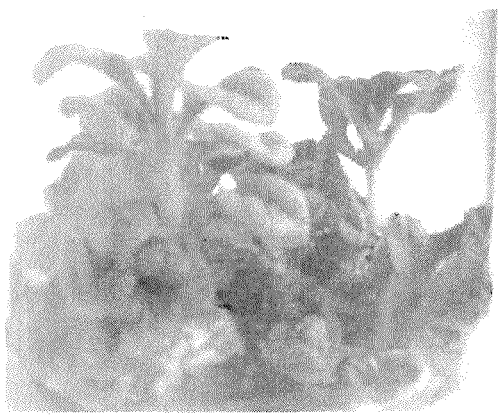
Figure 3:

FIG. 2, FIG. 3 and FIG. 4 depict eukaryotic cell expression of the expression vector containing the nucleotide sequence of SEQ ID NO:2 in tobacco cells. FIG. 2 depicts the growth state of the transgenic tobacco in MS2 medium, wherein the transgenic tobacco grew well. FIG. 3 depicts the root growth state of the transgenic tobacco (both negative and positive seedlings) in MS3 medium, wherein the roots of the transgenic tobacco grew well. FIG. 4 depicts the growth state of the transgenic sterile seedlings after they were transferred to perlite, wherein the transgenic sterile seedlings grew well.

FIG. 5 depicts the Northern blot analysis of some positive transgenic tobaccos that were confirmed by PCR detection. The hybridization results indicate that the nucleotide sequence of SEQ ID NO:2 can be expressed in the transgenic tobaccos.

FIG. 6 and FIG. 7 depict the salt and drought tolerance of the transgenic plants containing the nucleotide sequence of SEQ ID NO:2. FIG. 6 depicts the comparison between the transgenic tobaccos and the non-transgenic tobaccos in the medium with 0 mmol NaCl, and FIG. 7 depicts the comparison between the transgenic tobaccos and the non-transgenic tobaccos in the medium with 250 mmol NaCl after 15 days of culturing. The results shown in FIG. 7 indicate that the transgenic tobaccos grew normally in the medium with 250 mmol NaCl, while the non-transgenic tobaccos did not grow in the medium with 250 mmol NaCl.

THE EMBODIMENTS

The following examples are provided to further describe representative embodiments of the invention. It should be understood that the examples are intended to illustrate the methods of the invention and aren't intended to limit the scope of the invention. Any experiment conditions not described are according to the conventional conditions well known in the art, for example, the conditions described in Sambrook et al., Molecular Cloning: Laboratory Manual (New York: Cold Spring Harbor Laboratory Press, 1989), or according to the conditions recommended by the manufacturers.

Example 1

Expression of the Nucleotide Sequence of SEQ ID NO:1 in *E. coli* and Characterization of the Salt and Drought Tolerance Phenotype 1. Cloning of the Nucleotide Sequence of SEQ ID NO:1

Based on the published genome sequences of *Deinococcus radiodurans*, a pair of PCR specific primers were designed, and the complete nucleotide sequence of SEQ ID NO:1 was amplified from the genomic DNA of *Deinococcus radiodurans*.

2. Construction of an *E. coli* Expression Vector and its Molecular Verification The above amplified fragment was digested with two enzymes, NdeI and SacII, and ligated to the vector pTtSacB containing the *E. coli* universal promoter groE to replace the SacB gene and produce the *E. coli* expression vector. *E. coli* JM109 cells were transformed with the *E. coli* expression vector, and plated onto the LB solid medium containing Amp. The white colonies were selected, and plasmid DNA was extracted using the alkaline lysis method to screen the different recombinants. Plasmid DNA was digested with BglII and further characterized by sequencing. One strain of *E. coli* JM109 containing the above constructed expression vector was obtained. Restriction enzyme digestion confirmed that the fragment containing the groE promoter is 1.2 kb.

Figure 1:
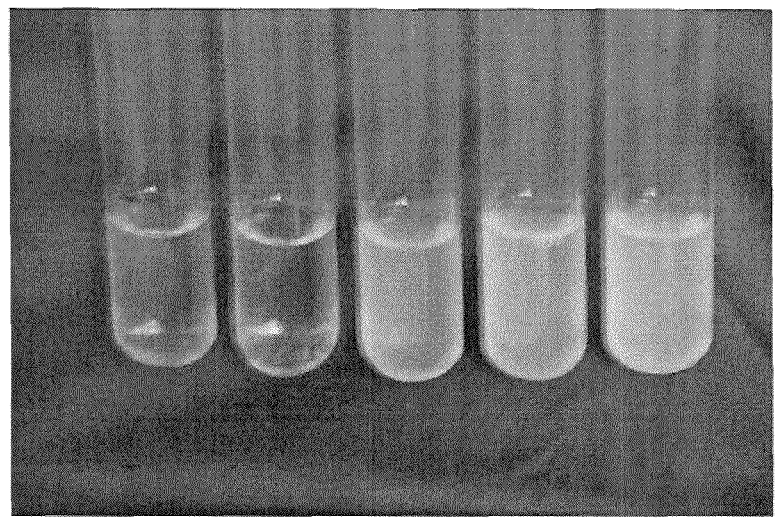
FIG. 1 depicts the growth state of *E. coli* containing the SEQ ID NO:1 expression vector in the medium containing 0.75M NaCl, showing that expression of SEQ ID NO:1 is capable of improve salt and drought resistance. The contents in 5 tubes in the figure are as follow.

3. Characterization of Salt and Drought Tolerance of the *E. coli* Expression Vector The *E. coli* JM109 strain containing the SEQ ID NO:1 nucleotide sequence expression vector, the *E. coli* JM109 strain containing pMD18T, and the host strain *E. coli* JM109 as controls, each of which had the same OD value, were inoculated at a 1% inoculum into the MM medium with 0.75M NaCl. The bacteria were cultured at 37° C. for 15 hours with shaking, and OD values were detected at 550 nm. As shown in FIG. 1, the *E. coli* JM109 strain containing the SEQ ID NO:1 nucleotide sequence expression vector tolerated 0.75M NaCl and grew well, whereas the *E.coli* JM109 strain only containing the empty expression vector and the host *E. coli* JM109 strain did not grow in the medium with 0.75M NaCl.

Example 2

The Artificial Synthesis of the SEQ ID NO:2 Nucleotide Sequence

The known SEQ ID NO:1 nucleotide sequence was divided into 7 regions. Single-stranded oligonucleotide fragments, each of which is 150-200 bp in length and has cohesive terminus, were synthesized according to the positive and negative strand sequences. The 7 pairs of complementary single-stranded oligonucleotide fragments corresponding to the positive strand and the negative strand were annealed to form 7 double-stranded oligonucleotide fragments with cohesive termini. The double-stranded oligonucleotide fragments were mixed, and assembled into a complete gene via T4 ligase. The synthesized DNA fragment contains XbaI and SacI sites at each of its ends.

The above synthesized SEQ ID NO:2 nucleotide sequence, having XbaI and SacI enzyme cleavage sites at the 5' and 3' ends, respectively, was used to construct the plant expression vector with high salt and drought tolerance as described below.

Example 3

The Eukaryotic Cell Expression of the Nucleotide Sequence of SEQ ID NO:2 in the Tobacco Cells and Characterization of the Salt and Drought Tolerance of the Transgenic Plants (1) The Construction of the Expression Vector Containing the Gene of Interest The primers for amplifying the complete coding reading frame were designed according to the full-length coding sequence (SEQ ID NO:2), and restriction enzyme cleavage sites were introduced into both the forward and the reverse primers (depending to the vectors selected) to facilitate the construction of the expression vector. The amplified product from Example 2 was used as the template to amply the sequence of cDNA, which was first cloned into an intermediate vector (such as pBluescript®) and further cloned into a binary expression vector, such as pBI121 and pCAMBIA2200. The desired expression vector was verified for its correct reading frame. The expression vector was transformed into *Agrobacterium*, and then transformed into the model plant tobacco using the leaf disc cocultivation method.

(2) Transformation of Tobacco Using the Leaf Disc Cocultivation Method 1. used sterile toothpicks to pick positive colonies from the selective YEB plate, inoculated into 2 ml YEB liquid (Sm+, Kan+), cultured for 24-36 hours at 28° C., with shaking at 200 rpm;
2. centrifuged at 4,000 g at room temperature for 10 min;
3. discarded the supernatant, suspended the bacteria with 1/2 MS medium, and diluted 5-20 times to obtain a bacterial suspension having an OD600 of about 0.5;
4. took a sterile leaf of tobacco that had been grown for about two weeks, removed the main vein, cut it into small pieces of about 1 cm$^2$;
5. placed the leaf pieces into the prepared bacterial suspension, immersed for 2-5 min, and absorbed the bacterial suspension liquid on the sterile filter paper;
6. placed the infected leaf pieces onto the MS medium and incubated for 48 hours at 28° C. in the dark;
7. transferred the leaf pieces onto the Callus medium (MS+ 6–BA 1.0 mg/L+NAA 0.1 mg/L+Kan 50 mg/L+cb 250 mg/L), incubated at 25-28° C. in the light and observed the formation of the callus tissues after 7-15 days;
8. observed the development of the differentiated buds after about 20 days, cut the buds after they grew up, put them into the root medium (1/2 MS+NAA 0.5 mg/L+Kan 25 mg/L) to perform rooting culture and observed the development of the roots after about 2-7 days;
9. removed the plant after the root system was fully developed, washed off the attached solid medium with sterile water, transferred the plant into the soil, initially covered it with a glass cover for several days, removed the cover after the plant was robust and planted it in the greenhouse. FIG. 2 depicts the growth state of the transgenic tobacco in MS2 medium, wherein the transgenic tobacco grew well; FIG. 3 depicts the root growth state of the transgenic tobacco (both negative and positive seedlings) in MS3 medium, wherein the roots of the transgenic tobacco grew well; and FIG. 4 depicts the growth state of the transgenic sterile seedlings after they were transferred to perlite, wherein the transgenic sterile seedlings grew well.

(3). Detection of the Expression of SEQ ID NO:2 in the Transgenic Tobacco Using Northern Blot 1. extracted RNA according to "molecular cloning" (Sambrook et al., 1989).
2. quantified RNA according to "molecular cloning" (Sambrook et al., 1989), measured the $OD_{260}$ using a spectrophotometer, calculated the amount of RNA based on 1 $OD_{260}$=40 µg/ml.
3. isolated the total RNA through agarose gel electrophoresis: 1) took 6 ml 25*electrophoretic buffer, added 117 ml sterile water into it and mix. 2) weighed 1.5 g agarose into the solution as above, heated it to melt in the micro oven, and transferred it to the water bath at 55° C. 3) took 26.8 ml formaldehyde in a fume cupboard, added it into the gel solution at 55° C. and mixed thoroughly. 4) poured it rapidly into the plate for making gel, stood horizontally at the room temperature for 30 mins to make the gel set. 5) dissolved 30 µg extracted RNA in 15 µl RNA dilute solution, heated it at 55-65° C. for 10 min and then immediately put it onto the ice. 6) added 2 µl 10*loading buffer into the sample and mix. 9) loaded the sample under the condition that the electrophoresis buffer did not cover the gel, started electrophoresis at 80 v for 10 min, added the electrophoresis buffer to exceed the surface of the gel about half-centimeter after the sample completely entered the gel. continued electrophoresis at 80-100 V for 5 hours.

4. transferred RNA onto the nylon membrane: 1) immersed the nylon membrane into 10*SSC before the transfer. 2) placed the wetted membrane correctly onto the gel, immersed two pieces of filter paper of the same size of the membrane into 2*SCC solution to wet, put them onto the membrane and removed any air bubble in between. 3) placed a pile of cleaning paper of the same size of the membrane onto the filter paper, put a piece of glass and a heavy object onto the cleaning papers, stood horizontally to transfer for 12-20 hours. 4) dried the membrane at 80° C. for 1-2 hours after transfer.
5. detected RNA on the membrane: 1) immersed the membrane in 4*SSC for 10 min, removed the membrane to put it onto the filter paper to absorb the excess liquid, put the membrane into prehybridization solution (50% formamide, 5*SSC, 50 mmol/L sodium phosphate (pH 6.4), 5*Denhardt's, 0.1% SDS, 0.1 mg/ml salmon sperm DNA), prehybridized at 42° C. overnight. 2) removed the prehybridization solution, replaced it with the same volume of hybridization solution, put DNA probe labeled with 32P into the boiling water to denature for 5 min, added it to hybridization solution (50% formamide, 5*SSC, 50 mmol/L sodium phosphate (pH 6.4), 10% dextran sulfate, 5*Denhardt's, 0.1% SDS, 0.1 mg/ml salmon sperm DNA), hybridized at 42° C. for 24-48 hours. 3) removed the membrane, put it into wash buffer I (1*SSC, 1% SDS), washed it three times at 42° C., 5 min every time. transferred it into wash buffer II (0.1*SSC, 1% SDS), washed it one to three times at 55-65° C. Pressed the X-ray film onto the membrane for 1-7 days, developed and fixed the film. FIG. 5 depicts the Northern blot analysis of some positive transgenic tobaccos that were confirmed by PCR detection. The hybridization results as shown in FIG. 5 indicate that the nucleotide sequence of SEQ ID NO:2 can be expressed in the transgenic tobaccos.

(4) Characterization of Salt and Drought Tolerance of the Transgenic Plants Containing the Nucleotide Sequence of SEQ ID NO:2

Given the above improved salt tolerance in *E. coli* expressing the nucleotide sequence of SEQ ID NO:1, the salt and drought tolerance of the transgenic plants was further characterized.

The transgenic tobacco and non-transgenic tobacco were cultured in the medium with 0 mmol or 250 mmol NaCl, and the viability and development of the plants were observed at 5 d, 10 d and 15 d. As shown in FIG. 6 and FIG. 7, the transgenic plants grew normally in the medium with 250 mmol NaCl, whereas non-transgenic tobacco did not grow in the same medium. The above results indicate that the sequence is capable of improving salt tolerance.

The invention claimed is:

1. A recombinant vector comprising an expression cassette comprising a nucleic acid molecule encoding the protein of SEQ ID NO: 3 operably linked to a plant promoter.

2. The recombinant vector of claim 1, wherein the nucleic acid molecule comprises SEQ ID NO: 1 or SEQ ID NO: 2.

3. A host cell comprising the recombinant vector of claim 1, wherein the host cell is a prokaryotic cell or a eukaryotic cell.

4. A method for producing a transgenic plant having improved salt and drought tolerance comprising the steps:
   (1) operatively linking a nucleic acid molecule encoding a protein having the amino acid sequence of SEQ ID NO: 3 with a plant expression regulation sequence to form a plant expression vector;
   (2) transforming the plant expression vector of step (1) into plant cells;
   (3) screening the transformed plant cells to obtain plant cells comprising the nucleic acid molecule encoding the protein having the amino acid sequence of SEQ ID NO: 3;
   (4) regenerating the plant cells obtained in step (3) into a transgenic plant, a seed thereof, a tissue thereof, or a progeny thereof, wherein said seed, tissue, or progeny comprises the plant expression vector; and
   (5) selecting the transgenic plant, seed, tissue or progeny of step (4) for improved salt and drought tolerance when compared to a non-transformed plant, seed, tissue or progeny.

5. The method of claim 4, wherein the nucleic acid molecule encoding the protein having the amino acid sequence of SEQ ID NO:3 comprises the nucleic acid sequence of SEQ ID NO: 1 or SEQ ID NO: 2.

6. A transgenic plant comprising a nucleic acid molecule encoding the protein having the amino acid sequence of SEQ ID NO:3, wherein said plant has improved salt and drought tolerance when compared to a non-transformed plant.

7. The transgenic plant of claim 6, wherein the nucleic acid molecule comprises SEQ ID NO: 1 or SEQ ID NO: 2.

* * * * *

SEQUENCE LISTING

<160> NUMBER OF SEQ ID NOS: 3

<210> SEQ ID NO 1
<211> LENGTH: 933
<212> TYPE: DNA
<213> ORGANISM: Deinococcus radiodurans

<400> SEQUENCE: 1

```
atgggccaa aagctaaagc tgaagcctcc aagccccacc cccaaatccc tgttaagctc      60
ccattcgtga ccgcccccga cgccctcgcc gccgccaaag ccaggatgcg cgacctggcg    120
gcggcctacg tggcggccct gcccggacgc gacacccaca gcctgatggc ggggggtgccc   180 ggcgtagacc tcaaattcat gccgctcggc tggcgcgacg gggcgttcga ccccgagcac    240
aacgtcatcc tcatcaactc ggcggcccgc cccgaacgcc agcgcttcac cctcgcccac    300
gaaatcgggc acgcgatttt actcggcgac gacgacctgc tctccgacat ccacgacgcc    360 tacgaggcg agcggctcga acaggtcatc gaaacgctgt gcaacgtggc ggcggcgcg     420 attttgatgc ccgaacccgt catcgcggaa atgctggaac gcttcggccc cacgggcgc    480 gccctcgccg aactcgccaa gcgggccgaa gtcagcgcgt cgtcggcgct ctacgccctg    540
accgagcaga ccccggtgcc cgtcatctac gcggtctgtg cgccgggcaa gcctccgcgt    600
gagcaggccg caagcgacga ggacgctggc ccaagcacag aaaaagtcct gacggtccgc    660
gccagcagct cgacgcgggg cgtcaagtac accctggcga gcggcacgcc ggtacccgcc    720 gaccaccccgg cggcgcttgc cctcgccacg ggcatggaag tgcgcgagga aagctacgtg    780
ccctttcgct cgggccggaa aatgaaggcg gaggtggacg cctacccgtc gcgcggcatc    840
gtggccgtca gtttcgagtt cgaccccgcc cgcctgggcc gcaaggacag cgagcaggcc    900
gaccgggacg agccgcagga cgctgcacag tga                                  933
```

<210> SEQ ID NO 2
<211> LENGTH: 933
<212> TYPE: DNA

<213> ORGANISM: Artificial
<220> FEATURE:
<223> OTHER INFORMATION: synthetic construct

<400> SEQUENCE: 2

```
atgggtccaa aggctaaggc tgaggcttct aagccacatc cacaaattcc agttaagctt      60
ccattcgtta ctgctccaga tgctcttgct gctgctaagg ctagaatgag agatcttgct     120
gctgcttacg ttgctgctct tccaggaaga gatactcatt ctcttatggc tggagttcca     180
ggagttgatc ttaagttcat gccacttgga tggagagatg gagctttcga tccagagcat     240
aacgttattc ttattaactc tgctgctaga ccagagagac aaagattcac tcttgctcat     300
gagattggac atgctattct tcttggagat gatgatcttc tttctgatat tcatgatgct     360
tacgagggag agagacttga gcaagttatt gagactcttt gcaacgttgc tgctgctgct     420
attcttatgc cagagccagt tattgctgag atgcttgaga gattcggacc aactggaaga     480
gctcttgctg agcttgctaa gagagctgag gtttctgctt cttctgctct ttacgctctt     540
actgagcaaa ctccagttcc agttatttac gctgtttgcg ctccaggaaa gccaccaaga     600
gagcaagctg cttctgatga ggatgctgga ccatctactg agaaggttct tactgttaga     660
gcttcttctt ctactagagg agttaagtac actcttgctt ctggaactcc agttccagct     720
gatcatccag ctgctcttgc tcttgctact ggaatggagg ttagagagga gtcttacgtt     780
ccattcagat ctggaagaaa gatgaaggct gaggttgatg cttacccatc tagaggaatt     840
gttgctgttt ctttcgagtt cgatccagct agacttggaa gaaaggattc tgagcaagct     900
gatagagatg agccacaaga tgctgctcaa taa                                   933
```

<210> SEQ ID NO 3
<211> LENGTH: 310
<212> TYPE: PRT
<213> ORGANISM: Artificial
<220> FEATURE:
<223> OTHER INFORMATION: synthetic construct

<400> SEQUENCE: 3

```
Met Gly Pro Lys Ala Lys Ala Glu Ala Ser Lys Pro His Pro Gln Ile
1               5                   10                  15

Pro Val Lys Leu Pro Phe Val Thr Ala Pro Asp Ala Leu Ala Ala Ala
            20                  25                  30

Lys Ala Arg Met Arg Asp Leu Ala Ala Ala Tyr Val Ala Ala Leu Pro
        35                  40                  45

Gly Arg Asp Thr His Ser Leu Met Ala Gly Val Pro Gly Val Asp Leu
    50                  55                  60

Lys Phe Met Pro Leu Gly Trp Arg Asp Gly Ala Phe Asp Pro Glu His
65                  70                  75                  80

Asn Val Ile Leu Ile Asn Ser Ala Ala Arg Pro Glu Arg Gln Arg Phe
                85                  90                  95

Thr Leu Ala His Glu Ile Gly His Ala Ile Leu Leu Gly Asp Asp Asp
            100                 105                 110

Leu Leu Ser Asp Ile His Asp Ala Tyr Glu Gly Glu Arg Leu Glu Gln
        115                 120                 125

Val Ile Glu Thr Leu Cys Asn Val Ala Ala Ala Ile Leu Met Pro
    130                 135                 140

Glu Pro Val Ile Ala Glu Met Leu Glu Arg Phe Gly Pro Thr Gly Arg
145                 150                 155                 160

Ala Leu Ala Glu Leu Ala Lys Arg Ala Glu Val Ser Ala Ser Ser Ala
                165                 170                 175
```

-continued

```
Leu Tyr Ala Leu Thr Glu Gln Thr Pro Val Pro Val Ile Tyr Ala Val
            180             185             190

Cys Ala Pro Gly Lys Pro Pro Arg Glu Gln Ala Ala Ser Asp Glu Asp
        195             200             205

Ala Gly Pro Ser Thr Glu Lys Val Leu Thr Val Arg Ala Ser Ser Ser
    210             215             220

Thr Arg Gly Val Lys Tyr Thr Leu Ala Ser Gly Thr Pro Val Pro Ala
225             230             235             240

Asp His Pro Ala Ala Leu Ala Leu Ala Thr Gly Met Glu Val Arg Glu
            245             250             255

Glu Ser Tyr Val Pro Phe Arg Ser Gly Arg Lys Met Lys Ala Glu Val
            260             265             270

Asp Ala Tyr Pro Ser Arg Gly Ile Val Ala Val Ser Phe Glu Phe Asp
            275             280             285

Pro Ala Arg Leu Gly Arg Lys Asp Ser Glu Gln Ala Asp Arg Asp Glu
    290             295             300

Pro Gln Asp Ala Ala Gln
305             310
```